United States Patent [19]

Saito

[11] Patent Number: 5,180,235

[45] Date of Patent: Jan. 19, 1993

[54] IMPACT PRINTER WITH VARIABLE IMPACT AND REBOUND CONTROL

[75] Inventor: Tetsuya Saito, Yokohama, Japan

[73] Assignee: Canon Kabushiki Kaisha, Tokyo, Japan

[21] Appl. No.: 892,473

[22] Filed: Jun. 2, 1992

Related U.S. Application Data

[63] Continuation of Ser. No. 553,367, Jul. 17, 1990, abandoned, which is a continuation of Ser. No. 241,862, Sep. 8, 1988, abandoned.

[30] Foreign Application Priority Data

Sep. 22, 1987 [JP] Japan .................................. 62-239469

[51] Int. Cl.$^5$ .............................. B41J 9/42; B41J 9/48
[52] U.S. Cl. ................................. 400/167; 440/157.2; 101/93.02
[58] Field of Search .................. 400/157.2, 157.3, 166, 400/167; 101/93.02

[56] References Cited

U.S. PATENT DOCUMENTS

| | | | |
|---|---|---|---|
| 1,977,531 | 10/1934 | Sperry | 400/661.1 |
| 4,064,799 | 12/1977 | Babler | 101/93.02 |
| 4,407,193 | 10/1983 | Hall | 400/157.3 |
| 4,440,079 | 4/1984 | Dayger | 400/157.3 |
| 4,547,087 | 10/1985 | Heider | 400/157.3 |
| 4,558,965 | 12/1985 | Ueda | 400/157.3 |

FOREIGN PATENT DOCUMENTS

| | | | |
|---|---|---|---|
| 173677 | 10/1983 | Japan | 400/157.2 |
| 222866 | 12/1983 | Japan | 400/157.2 |
| 52373 | 2/1985 | Japan | 400/661 |
| 162672 | 8/1985 | Japan | 400/661 |
| 237975 | 10/1988 | Japan | 400/157.2 |

*Primary Examiner*—David A. Wiecking
*Assistant Examiner*—Steven S. Kelley
*Attorney, Agent, or Firm*—Fitzpatrick, Cella, Harper & Scinto

[57] ABSTRACT

An impact printer has a platen, a carriage movable in parallelism to the platen, a hammer carried on the carriage, driving means for protruding the hammer toward the platen, detecting means for detecting the speed of the hammer striking against the platen and returned therefrom, and control means for changing over the speed at which the hammer is protruded toward the platen in conformity with the result of the detection of the detecting means.

21 Claims, 4 Drawing Sheets

IMPACT PRINTER WITH VARIABLE IMPACT AND REBOUND CONTROL

This application is a continuation of application Ser. No. 07/553,367 filed Jul. 17, 1990, which is a continuation of application Ser. No. 07/241,862 filed Sep. 8, 1988, now both abandoned.

BACKGROUND OF THE INVENTION

1. Field of the Invention

This invention relates to an impact type printer using, for example, a daisy wheel or the like to effect printing.

2. Related Background Art

As one of the main types of electronic typewriters and printers, there is the so-called impact type printer which strike a type member such as a daisy wheel or the like by a printing hammer to thereby accomplish printing. In such an impact printer, there has been the problem that when impact is effected by the printing hammer, the time for which a solenoid is energized is constant and therefore the output of the hammer is also constant and between the initial stage and the stage after use, the type portion of the type band is worn to deteriorate the quality of print. To solve such a problem, it is known to select time tables in order to obtain a stable output of the printing hammer even if the printer is used for a long period of time, as is known from Japanese Patent Application Laid-open No. 58-58278. That is, this is a system in which the operating speed of the hammer in the printing direction thereof is detected by a detecting coil and one of two or more sets of energization time tables of the hammer is selected in conformity with the result of the detection of the detecting coil to control the output of the hammer.

Also, the impact type printer system has the advantage that a high quality of print is obtained, while it suffers from the disadvantage that the noise during printing is great. One of the causes of this noise is the impact sound produced when the printing hammer is returned to the standby position after printing and strikes against a stopper, and as a method of decreasing such sound, it is known from U.S. Pat. No. 4,744,684, etc. to effect the second power supply to the solenoid before the printing hammer strikes the stopper, thereby imparting a damping force to the hammer.

The applicant improved on such a prior-art system and proposed, in Japanese Patent Application No. 61-66008 (U.S. application Ser. No. 029,686), to detect the return speed of the hammer, and brake the recording hammer by a damping force conforming to result of the detection. Further, the applicant proposed, in Japanese Patent Application No. 61-216051 and Japanese Patent Application No. 61-224906 (U.S. application Ser. No. 094,894), to detect the return speed of the hammer and determine the timing for braking the recording hammer in conformity with the result of the detection.

In such system, the impact sound of the hammer is very effectively decreased if the printer is used within a certain temperature range.

However, when the environmental temperature becomes low and the platen becomes very hard, the repulsion force of the platen increases remarkably and the return speed of the hammer becomes very high, and this has led to the undesirable possibility that there is insufficient time to effect the second power supply to the solenoid before the hammer strikes the stopper and thus, the hammer cannot be braked.

That is, when the environmental temperature becomes low, the return speed of the hammer becomes very high and the timing for braking the hammer is too late with the result that the impact sound of the hammer becomes vehiment. Also, if the second power supply is effected when the hammer strikes against the stopper and is bounded thereby, there has been the undesirable possibility that they are compounded to result in multiplex printing.

SUMMARY OF THE INVENTION

It is an object of the present invention to overcome the above-noted disadvantages by detecting the return speed of the hammer to thereby infer the hardness of the platen and adjust the printing pressure in conformity therewith.

Other objects of the present invention will become apparent from the following detailed description of an embodiment thereof.

DESCRIPTION OF THE PREFERRED EMBODIMENT

An embodiment of the present invention will hereinafter be described with reference to the drawings.

Figure 1B:
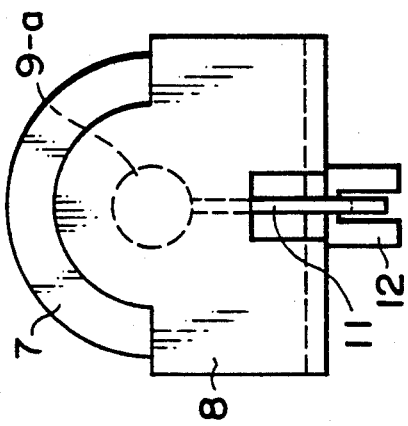
FIG. 1B is a rear view of the hammer mechanism portion shown in FIG. 1A.
Figure 1C:
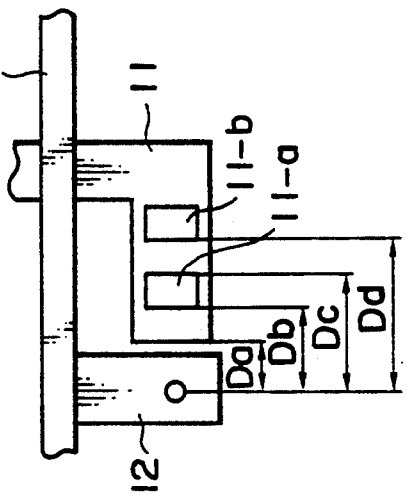
FIG. 1C is an enlarged view of the slit plate and the sensor portion shown in FIG. 1A.
Figure 1A:
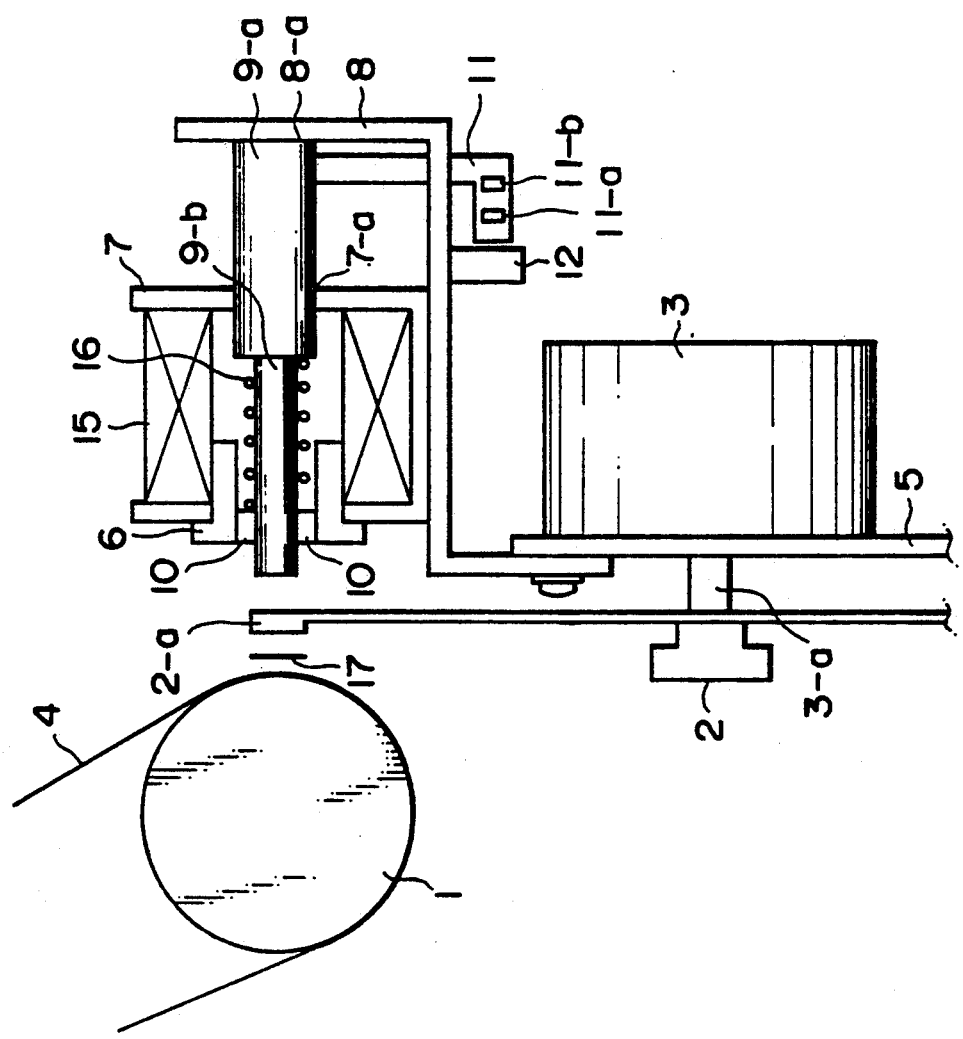
FIG. 1A shows the construction of a printer according to an embodiment of the present invention.

Referring to FIG. 1A which shows the construction of a printer, the reference numeral 1 designates a platen and the reference numeral 2 denotes a type wheel. The type wheel 2 is mounted on the shaft 3-a of a motor 3 and is rotated by rotation of the motor 3, and a type 2-a to be printed is carried to between a printing hammer 9 which will be described later and the platen 1. The motor 3 is fixed to a carriage 5. A hammer base 8 is attached to the carriage 5, and a hammer mechanism portion is provided on the hammer base 8. This hammer mechanism portion comprises a yoke 6, a support frame 7, a printing hammer 9, a bearing 10, a coil unit 15, a compression coil spring 16, etc. The printing hammer 9 comprises an armature 9-a formed of a magnetic material and a fore end portion 9-b formed of a non-magnetic material. The printing hammer 9 is supported by the bearing 10 and the bearing portion 7-a of the support frame 7 of the coil unit 15, and is movable in the thrust direction and is normally biased to the stopper 8-a of the hammer base 8 by the reaction force of the compression coil spring 16. That is, it is normally in its standby position. When an electric power is supplied to the coil unit 15, the printing hammer 9 is protruded toward the platen 1 by a magnetic force produced between the yoke 6 and the armature 9-a, and impacts the type 2-a against a recording medium 4 on the platen 1 through an ink ribbon 17, whereby printing is accomplished, and after printing, the printing hammer 9 is pushed back by the repulsion force of the compression coil spring 16 and strikes against the stopper 8-a and is stopped thereby, thus returning to its standby position. A slit plate 11 as shown in FIGS. 1 and 1C is provided on the printing hammer 9 and is reciprocally moved with the printing hammer 9. The slit plate 11 is provided with slits 11-a and 11-b and therefore, when the printing hammer 9 effects one cycle of reciprocal movement, a sensor 12 outputs a signal 19 as shown in FIG. 2.

Figure 2:
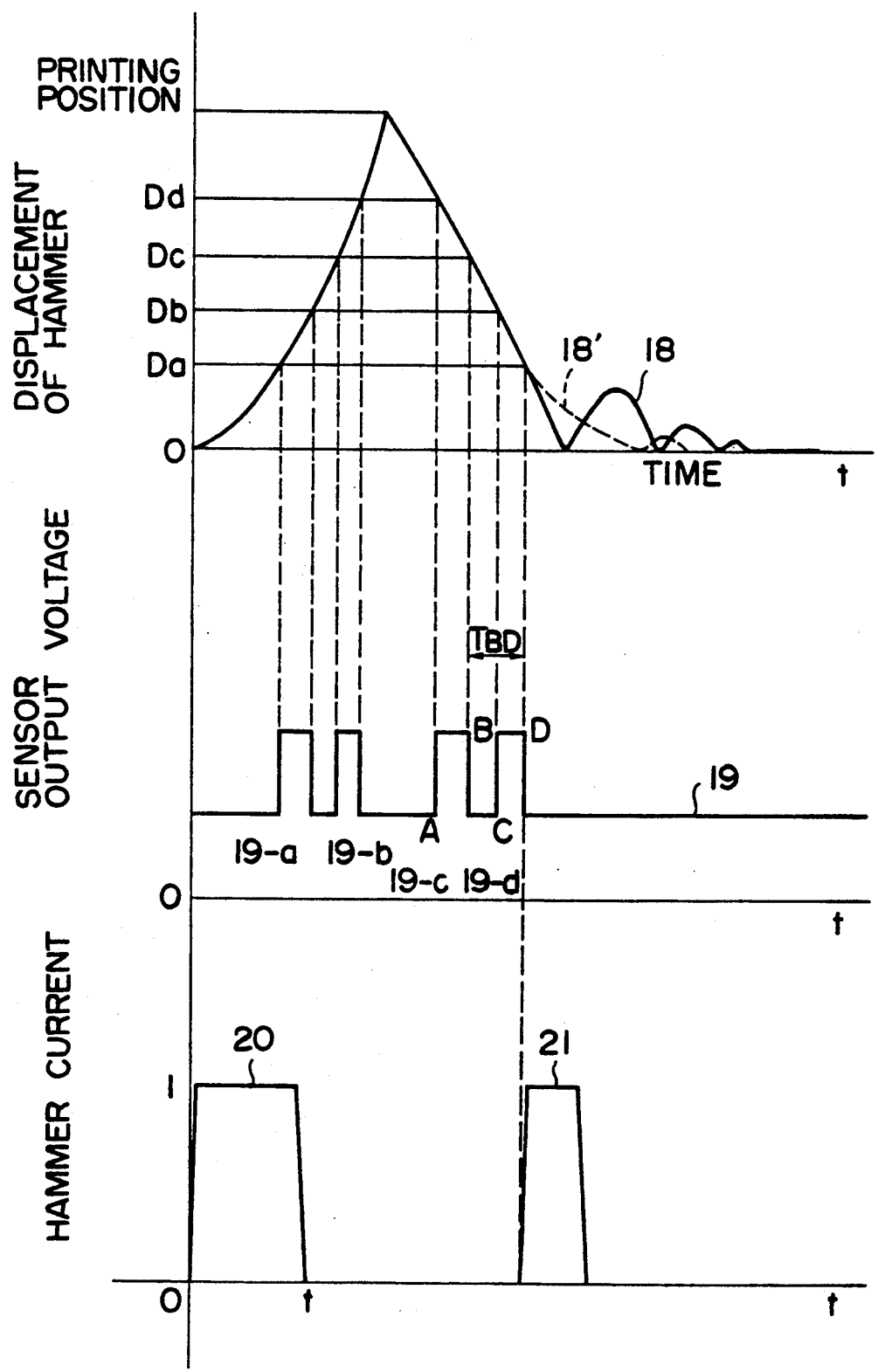
FIG. 2 is a graph showing the relation between the displacement of the hammer of FIG. 1 and the sensor output voltage.

Here, the curve 18 of FIG. 2 graphically shows the position of the printing hammer 9 for time. That is, in the figure, the printing hammer 9 is quickly protruded with the first power supply and arrives at the printing position. When the first power supply is terminated, the printing hammer 9 is returned rearwardly by the repulsion force of the coil spring and strikes against the stopper 8-a and is vibrated several times.

The signals 19-a and 19-b of the aforementioned signal 19 of FIG. 2 are output signals during the forward movement of the printing hammer 9 from the standby position to the printing position, and the signals 19-c and 19-d are output signals during the backward movement of the printing hammer from the printing position to the standby position. Here, the slit width and the slit spacing are constant and therefore, if the time interval between the signals, for example, the time interval $T_{BD}$ between B and D, is read, the average speed of the printing hammer 9 is the meantime can be found. Also, if the mutual positional relations between the stopper 8-a and the sensor 12 and the slit 11-a are predetermined, the position of the printing hammer 9 relative to the stopper 8-a can also be detected. If in accordance with this information, the second power supply is effected when the printing hammer 9 has come to a suitable position during the backward movement thereof, a magnetic force produced thereby acts in the direction opposite to the direction of movement of the printing hammer 9 and therefore, the return speed of the printing hammer 9 is decreased.

In FIG. 2, a first pulse 20 is for effecting printing, and a magnetic force is produced thereby and the printing hammer 9 is thereafter returned to the standby position by the repulsion force of the platen 1 and the force of the compression coil spring 16, and if at that time, the time interval $T_{BD}$ of FIG. 2 is detected and a proper current value and a proper excitation time are selected thereby and the second power supply is effected to the coil unit 15 at a point of time whereat the printing hammer 9 passes through D, the printing hammer 9 is decelerated by this magnetic force and slowly strikes against the stopper 8-a. This is shown by the curve 18' of FIG. 2. Thereby the impact sound between the printing hammer 9 and the stopper 8-a is greatly reduced and thus, the noise during printing can be reduced.

Further in the present embodiment, the return speed of the printing hammer 9 is detected, whereby the next protrusion speed of the printing hammer 9 is controlled. That is, generally, the platen is made of an elastic material such as rubber and when it is placed in a low temperature or when the hardening of the platen by a variation with time occurs, the repulsion coefficient thereof increases as compared with the usual case and therefore, even when printing is effected with the same printing energy, the return speed of the hammer shaft becomes high. So, the printing pressure may be changed over in conformity with the return speed detected by the sensor.

Figure 3:
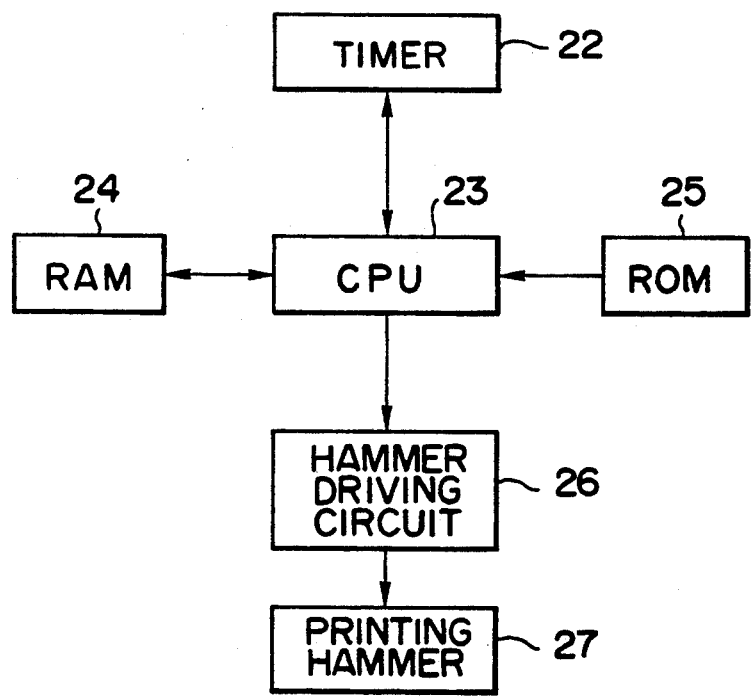
FIG. 3 is a block diagram showing the control circuit of the printing hammer shown in FIG. 1A.

FIG. 3 is a block diagram showing the printing hammer control circuit of the printer shown in FIG. 1. In the figure, the reference numeral 23 designates a CPU for controlling the recording apparatus. The CPU 23 has connected thereto RAM 22 for storing recording data or the like therein and ROM 24 storing therein a printing table or the like as shown in Table 1 below.

TABLE 1

| Printing pressure stage | Group | | |
|---|---|---|---|
| | 1 | 2 | 3 |
| Printing Pressure Table A (unit: m sec.) | | | |
| 1 | 5 | 9 | 11 |
| 2 | 10 | 12 | 15 |
| 3 | 15 | 17 | 19 |
| Characters and symbols | ., ., - | o, u, t | M, W |
| | (,) | 1, 7 | #, Ö |
| Printing Pressure Table B (unit: m sec.) | | | |
| 1 | 3 | 6 | 8 |
| 2 | 7 | 9 | 12 |
| 3 | 11 | 14 | 16 |
| Characters and symbols | ., ., - | o, u, t | M, W |
| | (,) | 1, 7 | #, Ö |

A timer 22 measures the time interval $T_{BD}$ between B and D in FIG. 2 and supplies the information to the CPU 23. A hammer driving circuit 26 is controlled by the CPU 23 in accordance with the recording data stored in RAM 24 and the printing table in ROM 25, and drives a printing hammer 27.

Figure 4:
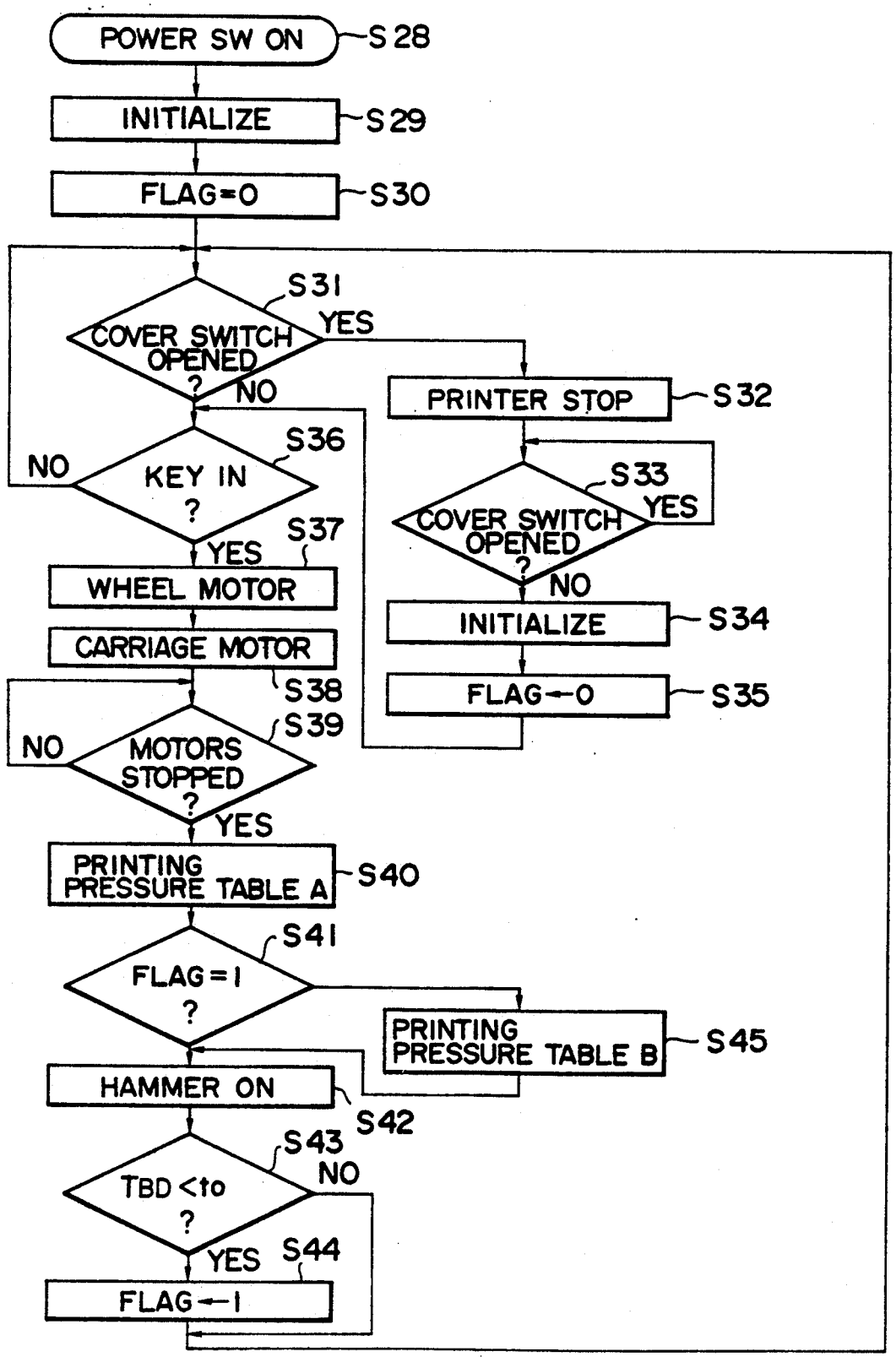
FIG. 4 is a flow chart showing the control operation of the printer shown in FIG. 1A.

FIG. 4 is a flow chart showing an example of the printer control based on the above-described construction. When a power switch is closed, initialization is effected and thereafter, a flag is set to 0 (steps S28-S30), and after the opening of a cover switch is detected (steps S31-S35), a standby condition for a key input is assumed (step S36). When the key input is effected thereafter, the wheel motor and the carriage motor are controlled (steps S37, S38 and S39), whereafter the printing pressure table A (see Table 1) is drawn out (Step S41). Subsequently, whether the flag is 0 or 1 is discriminated (step S41), and if the flag is 0, the printing hammer is driven in accordance with the printing pressure table A to effect printing (step S42). Also, if at step S41, the flag is 1, the printing pressure table B (see Table 1) is drawn out and the printing hammer is driven in accordance therewith (steps S45 and S46).

The return speed of the printing hammer is detected as $T_{BD}$ by the timer, and where $T_{BD}$ is shorter than a preset time $t_0$, the flag is set to 1, whereafter the printing hammer returns to the standby condition for a printing command. This state of the flag being 1 is kept until the cover switch is opened (steps S43 and S44).

Description will now be made with this applied to the actual operation of the printer. When the power switch is closed and an input for printing is effected to the printer which has become capable of printing, the printing hammer is driven in accordance with the printing pressure table A because the flag is set to 0 during the initialization. If at this time, the platen is hardened by a variation in temperature, a variation with time, etc. and therefore the return speed of the hammer shaft becomes high with a result that $T_{BD}$ becomes smaller than $t_0$. The flag is set to 1. In this state, the printing hammer is driven in accordance with the printing pressure table B at the subsequent cycles, and this mode is not released until the cover switch is opened.

Generally, when the platen becomes hardened, the necessary printing energy becomes small and therefore, if as shown in Table 1, the printing pressure table B is set to a printing pressure lower than the printing pressure table A, the fact that the platen has become hardened is automatically detected and printing can be effected at a printing pressure corresponding thereto.

Although in the above-described embodiment, the case where there are two kinds of printing pressure tables has been taken as an example, printing can also be effected, of course, in accordance with this concept in a case where there are three or more kinds of printing pressure tables, and not the excitation time, but the driving current value can also be changed over. Further, in the present embodiment, the releasing of the mode is effected by the cover switch, but it is also possible to measure time by the timer and release the mode after a predetermined time has elapsed, or to count the frequency of driving of the printing hammer and release the mode when it is detected within a predetermined frequency that $T_{BD}$ does not become $t_0$.

As described above, in the present invention, the printing pressure is changed in conformity with the return speed of the hammer detected by detecting means and therefore, printing can be accomplished with optimum printing energy conforming to the hardness of the platen.

Accordingly, even if the platen becomes hardened by a low temperature and the repulsion force of the platen is increased, the printing energy is made optimum and therefore, it does not happen that it becomes too late to effect the second power supply before the hammer strikes against the stopper.

I claim:

1. A recording apparatus for recording on a recording medium, said apparatus comprising:
   an image holding member;
   impacting means for impacting said image holding member to record on the recording medium, said impacting means being movable between an impacting position and a standby position;
   driving means for driving said impacting means from said standby position to said impacting position, said driving means applying first and second drive forces for driving said impacting means to said impacting position and a third drive force applied between said first and second drive forces;
   discriminating means for discriminating whether said third drive force is applied to said impacting means as said impacting means returns from said impacting position to said standby position; and
   controlling means for controlling said drive means, wherein
   when said discriminating means discriminates that said third drive force is not applied to said impacting means, said control means controls said drive means to apply a second drive which is smaller than said first drive force.

2. A recording apparatus according to claim 1, wherein said impacting means strikes said image holding member which the recording medium is positioned between a platen end and an ink ribbon.

3. A recording apparatus according to claim 1, wherein said impacting means has a yoke, a hammer member, a coil unit and a compression spring.

4. A recording apparatus according to claim 1, wherein said image holding member has a character wheel having a plurality of character members.

5. A recording apparatus according to claim 1, wherein said rebound speed detecting means detects a rebound speed while said impact means returns from a recording position to the initial position.

6. A recording apparatus according to claim 1, wherein said controlling means has a CPU and a RAM and a ROM which are connected to said CPU.

7. A recording apparatus according to claim 1, wherein said controlling means changes the impact force by controlling a driving time of said impacting means.

8. A recording apparatus according to claim 1, wherein said controlling means controls a driving time of said impacting means by selecting from a time table to thereby change the impact force.

9. A recording apparatus according to claim 1, wherein said discriminating means detects the speed of said impacting means when said impacting means returns from said impacting position to said standby position and discriminates that said third drive force is not applied to said impacting means when the detected speed is greater than a predetermined value.

10. A recording apparatus according to claim 1, wherein said third drive force is applied to decelerate said impacting means when said impacting means returns from said impacting position to said standby position.

11. A recording apparatus for recording on a recording medium, said apparatus comprising:
    a platen;
    a character wheel having a plurality of character members;
    hammer means for striking a selected one of said character members against said platen through the recording medium and an ink ribbon, said hammer means being moveable between an impacting position and a standby position;
    drive means for driving said hammer means from said standby position to said impacting position, said drive means applying first and second drive forces for driving said hammer means to said impacting position and a third drive force applied between said first and second drive forces;
    discriminating means for discriminating whether said third drive force is applied to said hammer means as said hammer means returns from said impacting position to said standby position; and
    controlling means for controlling said drive means, wherein
    when said discriminating means discriminates that said third drive force is not applied to said hammer means, said control means controls said drive means to apply a second drive force which is smaller than said first drive force.

12. A recording apparatus according to claim 11, wherein said platen is comprised of materials such that it changes hardness in accordance with the ambient temperature and humidity.

13. A recording apparatus according to claim 11, wherein said controlling means changes the impact force by controlling a driving time of said drive means.

14. A recording apparatus according to claim 11, wherein said controlling means controls a driving time of said drive means by selecting from a time table to thereby change the impact force.

15. A recording apparatus according to claim 11, wherein said discriminating means detects the speed of said hammer means when said hammer means returns from said impacting position to said standby position and discriminates that said third drive force is not applied to said hammer means when the detected speed is greater than a predetermined value.

16. A recording apparatus according to claim 11, wherein said third drive force is applied to decelerate said hammer means when said hammer means returns from said impacting position to said standby position.

17. An image printer for recording on a recording medium to be recorded, said printer comprising:
  an image holding member;
  impacting means for impacting said image holding member to record on the recording medium, said impacting means being movable between an impacting position and a standby position;
  driving means for driving said impacting means from said standby position to said impacting position, said driving means applying first and second drive forces for driving said impacting means to said impacting position and a third drive force applied between said first and second drive forces;
  discriminating means for discriminating whether said third drive force is applied to said impacting means as said impacting means returns from said impacting position to said standby position; and
  controlling means for controlling said drive means, wherein
  when said discriminating means discriminating that said third drive force is not applied to said impacting means, said control means controls said drive means to apply a second drive force which is smaller than said first drive force.

18. An image printer according to claim 17, wherein said controlling means changes the impact force by controlling a driving time of said impacting means.

19. An image printer according to claim 17, wherein said controlling means controls a driving time of said impacting means by selecting from a time table to thereby change the impact force.

20. An image printer according to claim 17, wherein said discriminating means detects the speed of said impacting means when said impacting means returns from said impacting position to said standby position and discriminates that said third drive force is not applied to said impacting means when the detected speed is greater than a predetermined value.

21. An image printer according to claim 17, wherein said third drive force is applied to said decelerate said impacting means when said impacting means returns from said impacting position to said standby position.

* * * * *

UNITED STATES PATENT AND TRADEMARK OFFICE
CERTIFICATE OF CORRECTION

PATENT NO. : 5,180,235
DATED : January 19, 1993
INVENTOR(S) : Tetsuya Saito

It is certified that error appears in the above-identified patent and that said Letters Patent is hereby corrected as shown below:

COLUMN 1:

Line 17, "strike" should read --strikes--.

COLUMN 5:

Line 55, "drive" should read --drive force--.

COLUMN 8:

Line 3, "discriminating" (second occurrence) should read --discriminates--.

Signed and Sealed this

Twenty-first Day of December, 1993

Attest:

BRUCE LEHMAN

*Attesting Officer*  *Commissioner of Patents and Trademarks*